United States Patent [19]
Ehlert et al.

[11] Patent Number: 5,562,790
[45] Date of Patent: Oct. 8, 1996

[54] APPARATUS AND METHOD FOR ROTARY BONDING

[75] Inventors: Thomas D. Ehlert, Neenah; Norman R. Stegelmann, Appleton, both of Wis.

[73] Assignee: Kimberly-Clark Corporation, Neenah, Wis.

[21] Appl. No.: 443,996

[22] Filed: May 18, 1995

Related U.S. Application Data

[62] Division of Ser. No. 268,758, Jun. 29, 1994.

[51] Int. Cl.$^6$ .................................................. B32B 31/16
[52] U.S. Cl. ..................... 156/73.1; 156/290; 156/324;
156/555; 156/580.1; 156/580.2; 156/582;
100/93 RP; 100/160; 100/168; 100/176;
264/445
[58] Field of Search ............................ 156/73.1, 290,
156/324, 580.1, 580.2, 555, 582; 264/23,
442, 444, 445; 425/174.2; 228/1.1, 110.1;
100/155 R, 155 G, 160, 168, 176, 93 RP

[56] References Cited

U.S. PATENT DOCUMENTS

| | | | |
|---|---|---|---|
| 3,844,869 | 10/1974 | Rust, Jr. et al. | 156/358 |
| 3,902,236 | 9/1975 | Deem | 29/256 |
| 3,942,789 | 3/1976 | Townsend | 271/274 |
| 4,076,663 | 2/1978 | Masuda et al. | 260/17.4 |
| 4,149,335 | 4/1979 | Duescher | 43/42.53 |
| 4,286,082 | 8/1981 | Tsubakimoto et al. | 526/240 |
| 4,512,564 | 4/1985 | Alverth et al. | 271/274 |
| 4,619,451 | 10/1986 | Dodge | 271/274 |
| 4,701,240 | 10/1987 | Kraemer et al. | 156/555 |
| 4,704,116 | 11/1987 | Enloe | 604/385 A |
| 4,798,603 | 1/1989 | Meyer et al. | 604/378 |
| 5,096,532 | 3/1992 | Neuwirth et al. | 156/580.1 |
| 5,110,403 | 5/1992 | Ehlert | 156/580.1 |
| 5,142,931 | 9/1992 | Menahem | 74/471 |
| 5,147,343 | 9/1992 | Kellenberger | 604/368 |

*Primary Examiner*—James Sells
*Attorney, Agent, or Firm*—Jeffrey B. Curtin

[57] ABSTRACT

An apparatus and method for bonding at least two continuously moving substrate webs together is disclosed. The apparatus comprises a rotatable bonding roll which is located adjacent the substrate webs and configured to rotate about a bonding axis. A rotatable anvil roll has an anvil surface and is configured to rotate about an anvil axis to press the substrate webs against an outer peripheral bonding surface of the bonding roll thereby bonding the substrate webs together. The anvil roll is pivotally connected to a pivotal support mechanism which is configured to maintain the anvil surface in a substantially parallel relationship with the bonding surface. The pivotal support mechanism is configured to allow the anvil roll to pivot such that the anvil roll maintains a substantially constant force on the bonding surface of the bonding roll across the width of the anvil roll.

9 Claims, 6 Drawing Sheets

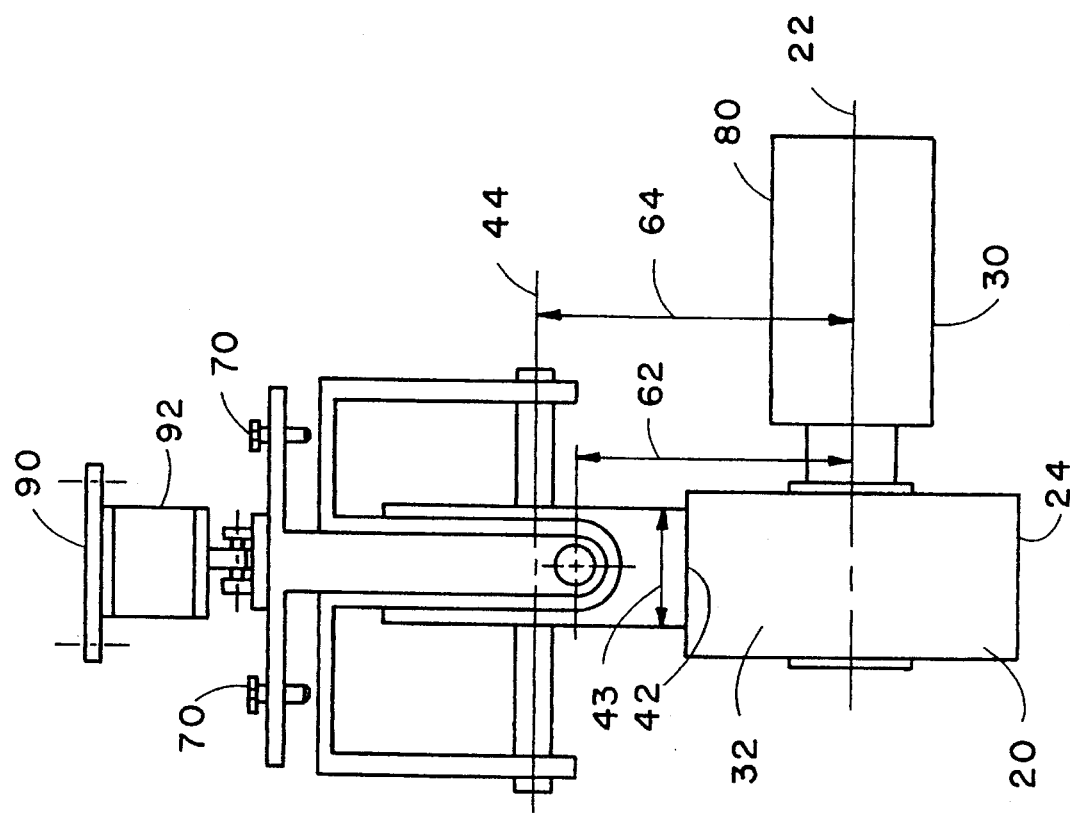
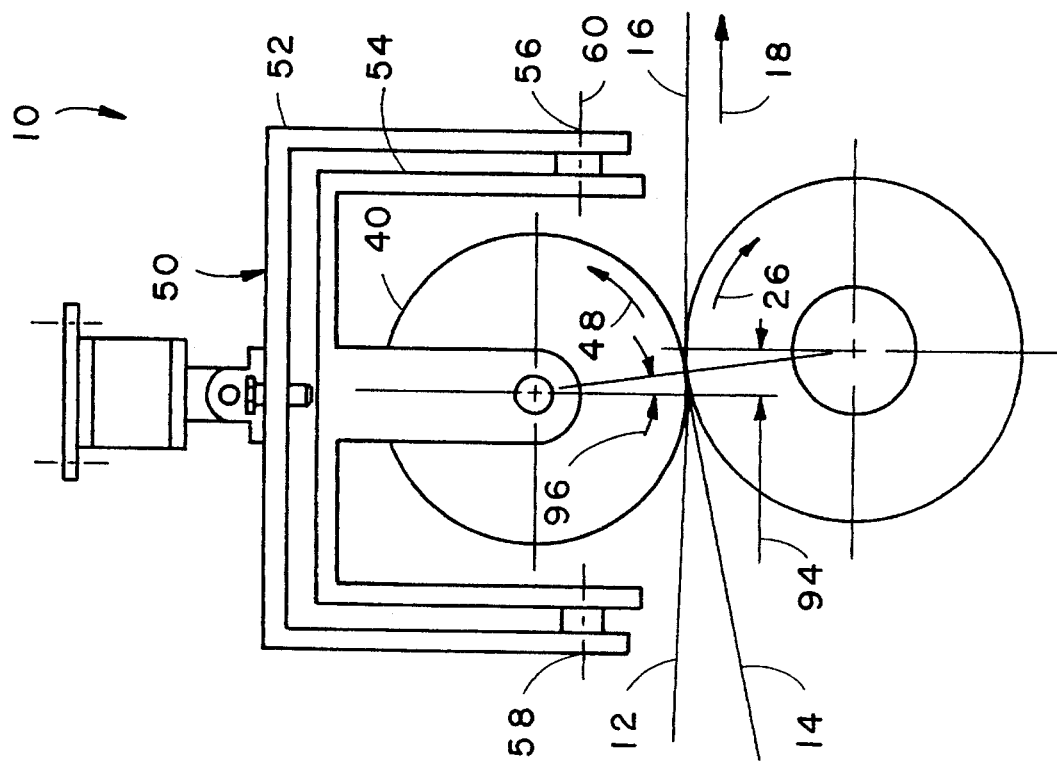

APPARATUS AND METHOD FOR ROTARY BONDING

This is a divisional application of copending application Ser. No. 08/268,758, filed on Jun. 29, 1994.

BACKGROUND OF THE INVENTION

1. Field of the Invention

The present invention relates to an apparatus and method for bonding at least two continuously moving webs together. The invention more particularly concerns an apparatus and method for ultrasonically bonding at least two continuously moving webs together using a rotary ultrasonic horn.

2. Description of the Related Art

Several different conventional methods have existed for bonding at least two continuously moving webs together. For example, it has been well known to those skilled in the art to bond two continuously moving substrate webs together by constrictively passing them between a rotating bonding roll and a rotating anvil roll. Typically, the anvil roll has been configured to bond the webs together in a predetermined bond pattern. The substrate webs have been bonded together by any means known to those skilled in the art such as thermal, ultrasonic or adhesive bonding. For example, the bonding roll has been heated to thermally bond the webs together as the webs constrictively travelled between the bonding roll and the anvil roll. Alternatively, the bonding roll has included a rotary ultrasonic horn which has been capable of transmitting ultrasonic energy to ultrasonically bond the two webs together as they constrictively travelled between the rotary ultrasonic horn and the anvil roll. Representative examples of rotary ultrasonic horns which have been used to bond at least two webs together are described in commonly assigned U.S. Pat. Nos. 5,096,532 to Neuwirth et al. and 5,110,403 to Ehlert.

The consistency and quality of the bonds between the webs when using rotary bonding techniques is dependent upon the force exerted on the webs by the anvil roll and bonding roll; the time that the webs are pressed together which is dependent upon the operating speed; and the types of materials being bonded together. In thermal bonding methods, the consistency and quality of the bonds has also been dependent on the temperature of the bonding roll. In ultrasonic bonding methods, the consistency and quality of the bonds has also been dependent on the frequency and amplitude of the vibrations of the ultrasonic horn.

Many of the conventional methods for rotary bonding have included a rotating anvil which is rigidly mounted. However, such conventional methods have not been sufficiently satisfactory. Although the use of a rigidly mounted, rotating anvil was a significant improvement in continuous bonding methods, such use has some inherent limitations which adversely affect the bond quality which, in turn, limits the operating speeds. When the rotating anvil is rigidly mounted, the consistency and quality of the bonds between the two webs is dependent upon the runout in both the bonding roll and the anvil roll and the amount that both rolls flex when under a variable load due to the types of materials being bonded and the variable operating speeds. In such a configuration, it has been virtually impossible to maintain proper alignment between the bonding roll and the anvil roll to achieve the desired constant force between the rolls in the bond region especially as the process variables change. Thus, in many of the conventional methods for rotary bonding, the bond quality has been undesirably variable both along the length and across the width of the bond region.

The consistency and quality of the bonds when rotary bonding using conventional methods has been particularly variable as the width of the desired bond pattern exceeds about 1 centimeter because it becomes increasingly difficult to maintain the constant force and contact between the bonding and anvil rolls across the entire width of the bond pattern. When using many of the conventional methods for rotary bonding in such a configuration, the actual percentage of the area of the webs being bonded together has been much less than the desired bond area based on the area of bond pattern on the anvil roll.

Many of the conventional methods for rotary bonding have used different approaches to diminish the extent of these limitations. For example, the bonding roll, anvil roll and support frames have been precisely machined to minimize the runout in the bonding system. In addition, the strength of the bonding and anvil rolls and their support frames has been increased to minimize the flexing under the variable load conditions. However, these approaches have been expensive and inefficient and have required extensive setup modifications as the process variables, such as operating speed, are changed.

The above-mentioned difficulties of maintaining the desired bond quality and consistency have been even more acute when ultrasonically bonding at least two continuously moving webs together using a rotary ultrasonic horn. The rotary ultrasonic horn has inherent movement which may adversely affect bond consistency and quality because it continuously vibrates at a given frequency and amplitude to efficiently bond the two webs together. Moreover, the rotary ultrasonic horn has usually been mounted in a cantilevered configuration which enhances the amount of flex under load.

SUMMARY OF THE INVENTION

In response to the discussed difficulties and problems encountered in the prior art, a new apparatus and method for rotary bonding has been discovered.

In an apparatus aspect, the present invention provides a distinctive apparatus for bonding at least two continuously moving substrate webs together. The apparatus comprises a rotatable bonding roll which is located adjacent the substrate webs and configured to rotate about a bonding axis. The bonding roll has an outer peripheral bonding surface upon which the substrate webs travel. A rotatable anvil roll having an outer peripheral anvil surface is located adjacent the bonding roll. The anvil roll is configured to rotate about an anvil axis to press the substrate webs against the bonding surface of the bonding roll thereby bonding the substrate webs together. The anvil roll is rotatably connected to a pivotal support means. The pivotal support means is configured to continuously align the anvil axis to maintain the anvil surface in a substantially parallel relationship with the bonding surface. The pivotal support means is configured to allow the anvil roll to pivot such that the anvil roll continuously maintains a substantially constant force on the outer peripheral bonding surface of the bonding roll across the width of the anvil roll.

In another apparatus aspect, the present invention provides an apparatus for ultrasonically bonding at least two continuously moving substrate webs together. The apparatus comprises an ultrasonic bonding means which provides ultrasonic energy. The ultrasonic bonding means includes a rotary ultrasonic horn which is configured to rotate about a bonding axis. The rotary ultrasonic horn has an outer peripheral bonding surface upon which the substrate webs travel. An anvil support frame is pivotally connected to a rigid frame at two pivot points located on a pivot axis. A rotatable anvil roll having an anvil surface is rotatably connected to the anvil support frame. The anvil roll is configured to rotate about an anvil axis and press the webs against the bonding surface of the rotary ultrasonic horn thereby bonding the substrate webs together. The anvil support frame is configured to pivot about the pivot axis to maintain the anvil surface in a substantially parallel relationship with the bonding surface of the rotary ultrasonic horn. In a particular aspect, the rotatable anvil roll has a plurality of projections across the anvil surface which are configured to bond the substrate webs together at bond locations which are arranged in a predetermined bond pattern. The bond pattern may have a width of at least about 1 centimeter.

A method aspect of the present invention provides a method for bonding at least two continuously moving substrate webs together. At least two continuously moving substrate webs are supplied along a substrate path. A rotatable bonding roll is provided adjacent the substrate path. The bonding roll is rotated about a bonding axis and has an outer peripheral bonding surface upon which the substrate webs travel. A rotatable anvil roll which has an outer peripheral anvil surface and an anvil width is also provided adjacent the substrate path. The anvil roll rotates about an anvil axis and presses the substrate webs against the bonding surface of the bonding roll thereby bonding the substrate webs together across the outer peripheral anvil surface of the anvil roll. The anvil roll is pivotally supported to continuously align the anvil axis to maintain the anvil surface in a substantially parallel relationship with the bonding surface. The anvil roll can maintain a substantially constant force on the outer peripheral bonding surface of the bonding roll across the width of the anvil roll. In a particular aspect of the method of the present invention, the bonding roll may comprise an ultrasonic bonding means which includes a rotary ultrasonic horn.

The present invention, in its various aspects, can advantageously provide an apparatus and method for rotary bonding which, when compared to conventional devices, can more efficiently bond two continuously moving webs together while maintaining a substantially constant bond pattern between the webs. The apparatus and method of the present invention automatically adjust the alignment between the bonding roll and the anvil roll to compensate for runout and the flex due to the variable loads thereby improving the bond quality and consistency. The apparatus of the present invention is also less expensive when compared to the conventional devices because lower precision components can be employed.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the appended claims.

FIG. 3A representatively shows a front elevational view of another example of an apparatus of the present invention;

FIG. 3B representatively shows a side elevational view of the apparatus illustrated in FIG. 3A;

DETAILED DESCRIPTION OF THE INVENTION

Figure 1B:
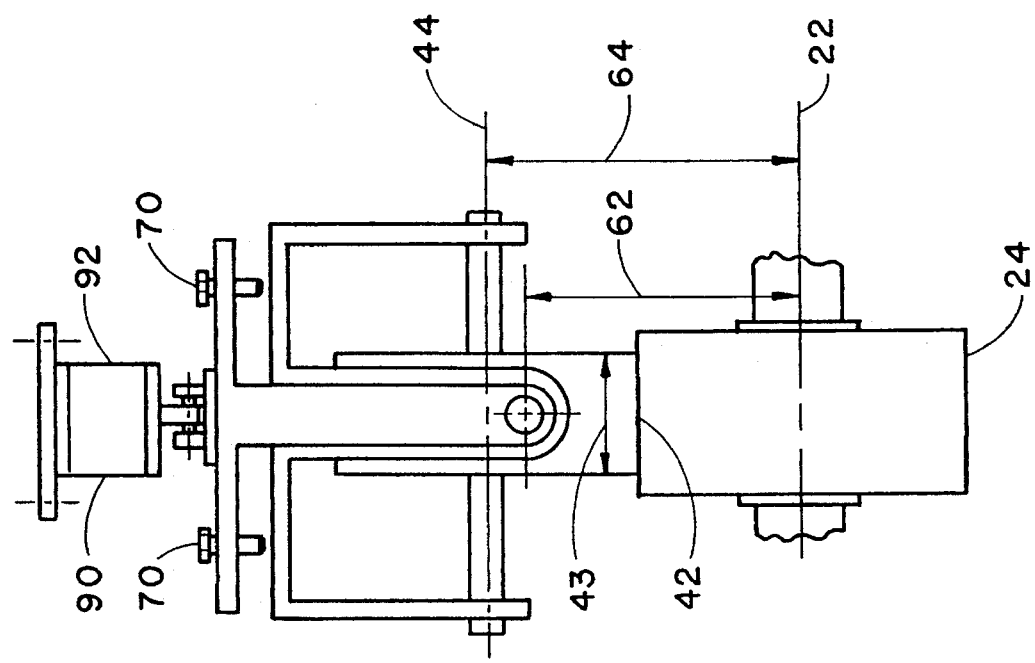
FIG. 1B representatively shows a side elevational view of the apparatus illustrated in FIG. 1A.
Figure 1A:
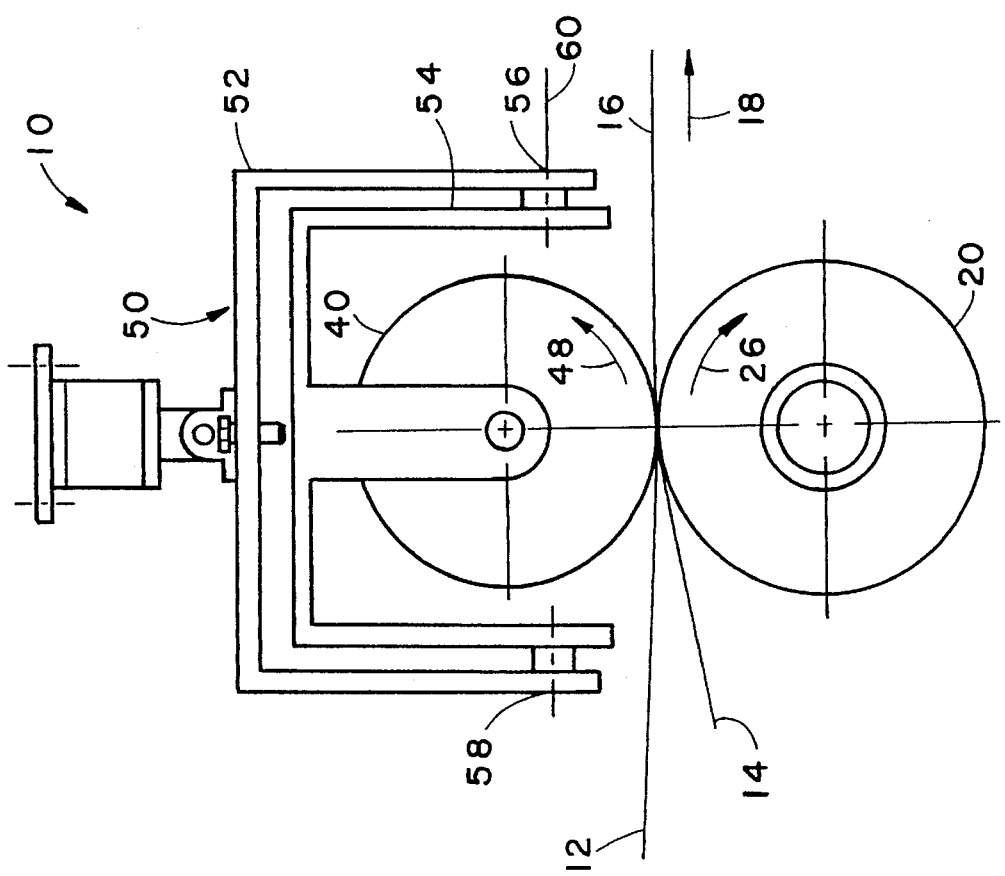
FIG. 1A representatively shows a front elevational view of one example of an apparatus of the present invention.
Figure 2B:
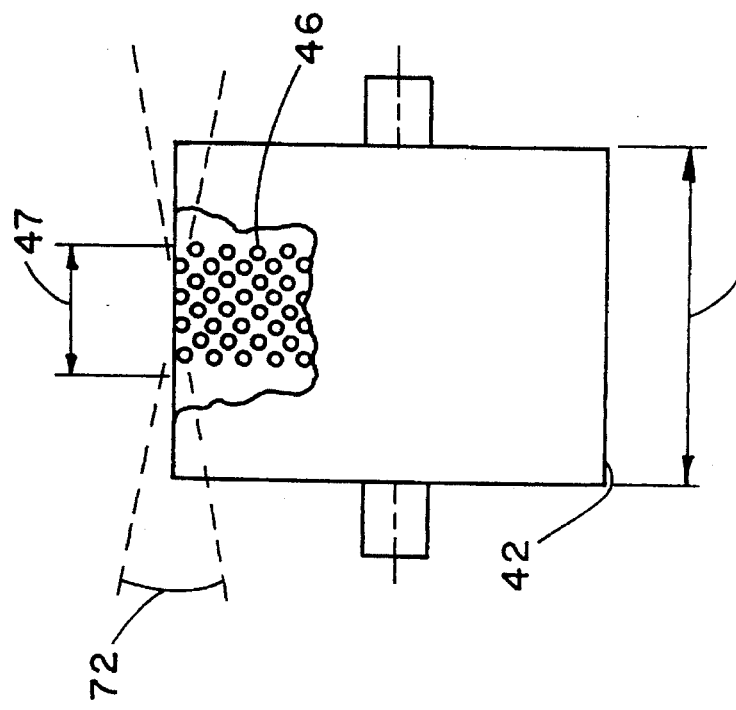
FIG. 2B representatively shows another example of an anvil roll of the apparatus of the present invention.
Figure 2C:
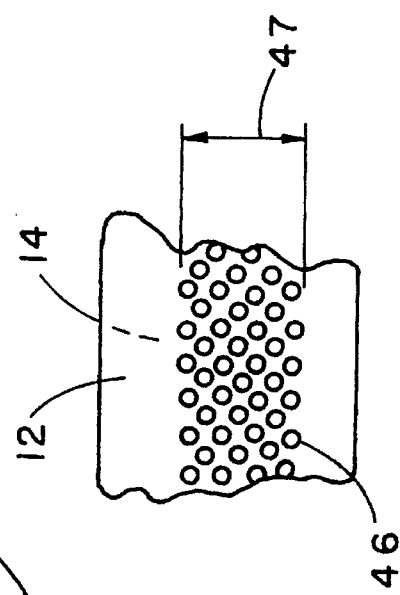
FIG. 2C representatively shows an example of a composite substrate web which is manufactured using the apparatus and method of the present invention.
Figure 2A:
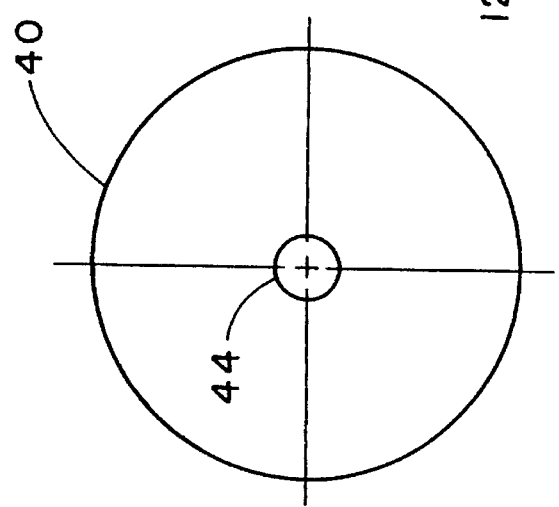
FIG. 2A representatively shows an example of an anvil roll of the apparatus of the present invention.

The present invention provides an apparatus and method for bonding at least two continuously moving substrate webs together. The apparatus and method are particularly useful for ultrasonically bonding selected components to absorbent articles using a rotary ultrasonic horn. Alternatively, the apparatus and method are useful for bonding two webs together to form a composite material and subsequently using it as a component in an absorbent article such as, for example, a disposable diaper. The present invention is particularly useful in the bonding of two or more layers of materials which preferably are made, at least in part, from thermoplastic polymers.

In particular, the apparatus and method of the present invention can be used to ultrasonically bond stretchable outer ears to a disposable diaper using a rotary ultrasonic horn. The stretchable outer ears enhance the fit of the diaper about the waist of the wearer. The apparatus and method of the present invention may also be used to bond a fastening system to the outer ears of the diaper. In addition, it should be readily understood that the apparatus and method of the present invention may be used in the manufacture of other types of articles, such as, for example, training pants, feminine care products, incontinence garments, hospital gowns and the like. All of such alternative configurations are contemplated as being within the scope of the present invention. The present invention may also be used to perforate a material such as, for example, using a rotary ultrasonic horn to selectively perforate a material.

Referring to the Figures wherein like numerals represent like elements, an apparatus and method for rotary bonding are representatively illustrated in FIGS. 1A–3B. The apparatus, which is generally indicated at 10, and method may be used to bond at least two continuously moving substrate webs 12 and 14 together. The substrate webs 12 and 14 are continuously moving along a substrate path 16 in the direction indicated by the arrow 18 associated therewith. The apparatus 10 includes a rotatable bonding roll 20 which is located adjacent the substrate webs 12 and 14. The bonding roll 20 is configured to rotate about a bonding axis 22 in the direction indicated by the arrow 26 associated therewith. The bonding roll 20 has an outer peripheral bonding surface 24 upon which the substrate webs 12 and 14 travel. A rotatable anvil roll 40 having an outer peripheral anvil surface 42 and an anvil width 43 is located adjacent the bonding roll 20. The anvil roll 40 is configured to rotate about an anvil axis 44 in the direction indicated by the arrow 48 associated therewith to press the substrate webs 12 and 14 against the bonding surface 24 of the bonding roll 20 thereby bonding the substrate webs together. The anvil roll 40 is rotatably connected to a pivotal support means 50. The pivotal support means 50 continuously aligns the anvil axis to maintain the anvil surface 42 in a substantially parallel relationship with the bonding surface 24. The pivotal support means 50 is configured to allow the anvil roll 40 to pivot such that the anvil roll 40 continuously maintains a substantially constant force on the outer peripheral bonding surface 24 of the bonding roll 20 across the anvil width 43 of the anvil roll 40.

The substrate webs 12 and 14 may be provided by any materials known to those skilled in the art which are compatible with the described bonding mechanisms. For example, the substrate webs 12 and 14 may include a nonwoven material such as a spunbond, meltblown, spun 1 aced or carded polymeric material, a film material such as a polyolefin or polyurethane film, a foam material or combinations thereof. For the purposes of the present description, the term "nonwoven web" shall mean a web of material which is formed without the aid of a textile weaving or knitting process. The substrate webs 12 and 14 may also be elastic or nonelastic such as films or layers of natural rubber, synthetic rubber or thermoplastic elastomeric polymers. As used herein, the terms "elastomeric" or "elastic" refer to any material that, upon application of a biasing force, is capable of being elongated or stretched in a specified direction from at least about 20 percent to about 400 percent and which will recover to within at least from about 5 to about 35 percent of its original length after being elongated or stretched. The substrate webs 12 and 14 may be the same material or may be different materials. In a specific aspect, at least one of the substrate webs is formed from an elastomeric material such as a stretch-bonded-laminate (SBL) material, a neck-bonded-laminate (NBL) material, an elastomeric film, an elastomeric foam material, or the like as are well known to those skilled in the art.

It should be apparent that adequate bonding can be achieved by a variety of mechanisms. For example, the bond can result from the partial or complete melting of the substrate webs 12 and 14. The bond can also result from the partial or complete melting of only one of the substrate webs 12 and 14 with the melted material flowing onto the adjacent substrate web which in turn results in the mechanical interlocking of the substrate webs to each other. The substrate webs 12 and 14 may be melted and bonded by any means known to those skilled in the art, such as, for example, thermally or ultrasonically. Alternatively, the substrate webs 12 and 14 may be adhesively bonded together by applying an adhesive to at least one of the substrate webs before the webs are pressed together using the apparatus and method of the present invention.

As representatively illustrated in FIGS. 1A-3B, the bonding roll 20 is configured to rotate about the bonding axis 22 in the direction indicated by the arrow 26 associated therewith. The bonding roll 20 can be connected to a shaft by suitable means such as by using welds, bolts, screws, a matching key and keyway and the like. The other rotating components of the apparatus 10 may also be connected using similar means. The bonding roll 20 and shaft may then be rotatably mounted and connected to a frame support by suitable means such as, for example, conventional bearings. Typically, the bonding roll 20 is driven by any means known to those skilled in the art such as, for example, an electric motor. The bonding roll 20 can be made from any material that is capable of withstanding the force exerted by the anvil roll 40. Desirably, the bonding roll is made from steel. In one aspect, the bonding roll 20 can be heated and configured to thermally bond the substrate webs 12 and 14 together.

In another aspect of the invention, the continuously moving substrate webs 12 and 14 are melted ultrasonically using a rotary ultrasonic horn and bonded together. As representatively illustrated in FIGS. 3A and 3B, the bonding roll 20 can include an ultrasonic bonding means 30 which can include a rotary ultrasonic horn 32. The anvil roll 40 is configured to rotate about the anvil axis 44 in the direction indicated by the arrow 48 associated therewith to press the substrate webs 12 and 14 against the bonding surface 24 of the rotary ultrasonic horn 32 thereby bonding the substrate webs together. The pivotal support means 50 is configured to allow the anvil roll 40 to pivot to continuously align the anvil axis 44 to maintain the anvil surface 42 in a substantially parallel relationship with the bonding surface 24 of the rotary ultrasonic horn 32.

In an alternative aspect of the present invention, the anvil roll 40 can include the ultrasonic bonding means 30 and rotary ultrasonic horn 32. In such a configuration, the rotary ultrasonic horn would press the substrate webs 12 and 14 against the bonding surface 24 of the bonding roll 20. The pivotal support means 50 would be configured to allow the rotary ultrasonic horn to pivot to continuously align the anvil axis 44 to maintain the anvil surface 42, or surface of the rotary ultrasonic horn, in a substantially parallel relationship with the bonding surface 24 of the bonding roll 20.

As representatively illustrated in FIGS. 3A and 3B, the rotary ultrasonic horn 32 of the different aspects of the present invention includes a shaped, solid metal object. Representative examples of rotary ultrasonic horns which can be used in the present invention are described in commonly assigned U.S. Pat. No. 5,096,532 to Neuwirth et al. and U.S. Pat. No. 5,110,403 to Ehlert, which are herein incorporated by reference. In general, the rotary ultrasonic horn 32 may be made from any metal having suitable acoustical and mechanical properties. Suitable metals include aluminum, monel, titanium and some alloy steels. In general, variables such as the diameter, mass, width, thickness and configuration of the rotary ultrasonic horn 32 are not critical. However, the variables do determine the particular frequency and amplitude at which the rotary ultrasonic horn 32 resonates and vibrates.

The rotary ultrasonic horn 32 is intended to be excited at a frequency of from about 18 to about 60 kHz. The horn 32 has a diameter of from about 4 to about 20 centimeters and a width at the bonding surface 24 of from about 0.6 to about 13 centimeters. The thickness of the horn at the rotational axis is from about 0.06 to about 15 centimeters. The horn has a mass in the range of from about 0.06 to about 30 kilograms. The diameter, width and thickness of the horn are selected such that the horn, upon being excited by ultrasonic energy at a desired frequency, is adapted to resonate such that the excited end moves substantially in phase with the movement of the source of excitation and the opposed end and bonding surface 24 move substantially out of phase with the excited end. Thus, upon subjecting the horn 32 to ultrasonic excitation, the excited end moves in a direction towards the interior of the horn while the opposing end and the bonding surface 24 move in the opposite direction which is also towards the interior of the horn. As such, the movements of the ends of the horn relative to each other are said to be out of phase.

The ultrasonic bonding means 30 also includes a drive mechanism 80 to rotate and ultrasonically excite the rotary ultrasonic horn 32. Any mechanism which provides the desired rotation and excitation can be used in the present invention. Such mechanisms are well known to those skilled in the art. For example, the ultrasonic bonding means 30 may include a drive mechanism 80 which is commercially available from Dukane Corporation located in St. Charles, Ill. or a similar system available from Branson Sonic Power Company located in Danbury, Conn. Typically, a generator, such as a Dukane 1800 watt, 20 kHz generator (Part No. 20A1800), is connected to a driver assembly, such as a Dukane driver assembly (Part No. 110-3123), to provide the necessary ultrasonic excitation. Any combination of boosters, such as a Dukane 1:1 booster (Part No. 2177T) and a Dukane 2:1 booster (Part No. 2181T), may then be attached to the driver assembly. Finally, the rotary ultrasonic horn 32 of the present invention is attached to the boosters. Thus, the combination of the generator, drive assembly and boosters ultrasonically excites the rotary ultrasonic horn 32 thereby providing the ultrasonic energy necessary to bond the substrate webs 12 and 14 together.

As representatively illustrated in FIGS. 1A–3B, the anvil roll 40 is configured to rotate about the anvil axis 44 and press the substrate webs 12 and 14 against the bonding surface 24 of the bonding roll 20, thereby bonding the substrate webs together. The anvil roll 40 is connected to a shaft which is rotatably mounted and connected to the pivotal support means 50 by any suitable means, such as conventional bearings. In general, the anvil roll 40 may be made from any metal having suitable mechanical properties. Suitable metals include alloy steels.

Typically, the anvil roll has an anvil surface 42 and an anvil width 43 of from about 1 to about 15 centimeters and desirably from about 3 to about 15 centimeters. The anvil surface 42 is configured to bond the substrate webs 12 and 14 together at bond locations which are arranged in a predetermined bond pattern. Applicants have found that as the width of the desired bond pattern and the corresponding anvil width 43 of the anvil roll 40 increases it becomes increasingly difficult to maintain the appropriate alignment between the anvil surface 42 and the bonding surface 24 when using a conventional anvil roll which is rigidly mounted. As representatively illustrated in FIG. 2B, the anvil surface 42 of the anvil roll 40 may have a plurality of projections 46 thereon. The projections 46 may extend completely across the anvil surface 42 of the anvil roll 40 or, in the alternative, may be disposed on only a portion of the anvil surface 42. The projections 46 of the anvil roll 40 press the substrate webs 12 and 14 against the bonding roll 20 to bond the substrate webs 12 and 14 together at bond locations. As representatively illustrated in FIG. 2C, the projections 46 of the anvil roll 40 can be configured such that the substrate webs 12 and 14 are bonded together at bond locations which are arranged in a predetermined bond pattern. The projections 46 may be of any shape or size depending upon the desired bonding configuration. In another aspect of the invention, the bonding surface 24 of the bonding roll 20 may also have a plurality of projections 46 thereon. The different aspects of the present invention are particularly useful when the width 47 of the bond pattern is at least about 1 centimeter, desirably from about 1 to about 13 centimeters and more desirably from about 2.5 to about 13 centimeters.

As representatively illustrated in FIGS. 1A–3B, the anvil roll 40 is rotatably mounted and connected to a pivotal support means 50 by any suitable means, such as conventional bearings. The pivotal support means 50 is configured to align the anvil axis 44 to maintain the anvil surface 42 in a substantially parallel relationship with the bonding surface 24. Thus, the pivotal support means 50 is configured to allow the anvil roll 40 to pivot such that the anvil roll is capable of self-aligning to continuously maintain a substantially constant force on the outer peripheral bonding surface 24 of the bonding roll 20. The force can be maintained substantially constant across the anvil width 43 of the anvil roll 40. In a particular aspect wherein the anvil roll 40 has a plurality of projections 46 thereon, the anvil roll is configured to maintain a substantially constant force on the outer peripheral bonding surface 24 of the bonding roll 20 at least substantially across the width of the projections 46 on the anvil roll 40.

As representatively illustrated in FIGS. 1A–3B, the pivotal support means 50 may include an anvil support frame 54 which is pivotally connected to a rigid frame 52 at two pivot points 56 and 58 which are located on a pivot axis 60. The anvil roll 40 is connected to a shaft which is located on the anvil axis 44 and rotatably mounted and connected to the anvil support frame 54. The pivot axis 60 is perpendicular to both the anvil axis 44 and the bonding axis 22 and substantially parallel to the direction the substrate webs are moving along the substrate path 16 at any particular location. The anvil support frame 54 includes a pivot shaft which is rotatably mounted and connected to the rigid frame 52 at the pivot points 56 and 58. The pivot shaft is connected to the rigid frame 52 using a pair of conventional bearings such that the anvil support frame 54 and anvil roll 40 pivot about the pivot axis 60. In such a configuration, the anvil roll 40 is capable of pivoting about the pivot axis 60 such that the anvil surface 42 is maintained in a substantially parallel relationship with the bonding surface 24. As such, the anvil roll 40 is configured to self-align to maintain a substantially constant force on the outer peripheral bonding surface 24 of the bonding roll 20 substantially across the entire anvil width 43 of the anvil roll 40.

The rigid frame 52 and anvil support frame 54 may have any shape or configuration which provides the desired pivoting of the anvil roll 40. The frames 52 and 54 may be made from any material capable of withstanding the forces exerted between the bonding roll 20 and anvil roll 40 during bonding. For example, a suitable material is steel. As representatively illustrated in FIGS. 1A–3B, the rigid frame 52 and anvil support frame 54 may both be u-shaped with the anvil roll 40 positioned in the interior portion of each frame 52 and 54. The conventional bearings can be mounted directly to the frames 52 and 54.

As representatively illustrated in FIGS. 1A–3B, the pivot axis 60 of the anvil support frame 54 is located a first distance 62 from the bonding axis 22 and the anvil axis 44 is located a second distance 64 from the bonding axis 22. In general, the second distance 64 is dependent upon the particular diameters of the bonding roll 20 and anvil roll 40. Desirably, the first distance 62 is less than the second distance 64 such that the pivot axis 60 is closer than the anvil axis 44 to the bonding axis 22. For example, the first distance 62 may be at least about 1 percent, desirably from about 1 to about 50 percent and, more desirably from about 5 to about 25 percent less than the second distance 64. In such a configuration, Applicants have found that the bonding roll 20 and anvil roll 40 are more stable during use thereby providing improved bonding between the substrate webs 12 and 14.

As representatively illustrated in FIGS. 1A–3B, the pivotal support means 50 of the apparatus and method of the present invention may also include at least one pivot stop 70 to control an amount of pivot 72 of the anvil support frame 54 and the anvil roll 40. As illustrated in FIG. 2B, the pivot stops 70 limit the amount of pivot 72 of the anvil roll 40 to from 0 to about 15 degrees.

The apparatus 10 and method of the present invention as representatively illustrated in FIGS. 1A–3B, may also include a pressuring means 90 connected to the anvil roll 40 for exerting resilient force on the substrate webs 12 and 14 and the bonding roll 20 to bond the substrate webs 12 and 14 together. The pressuring means 90 should be capable of exerting a force of from about 1 to about 300 and desirably from about 10 to about 150 pounds per lineal inch (from about 0.1 to about 55 and desirably from about 2 to about 27 kilograms per lineal centimeter) on the bonding roll 20. Any mechanism capable of exerting the desired amount of force on the webs and bonding roll is suitable. For example, an air cylinder 92 may be connected to the rigid frame 52. The air cylinder 92 may be configured to exert an actuating force on the rigid frame 52 which, in turn, transfers the force to the anvil support frame 54 through the pivot points 56 and 58. Desirably, the rigid frame 52 is controlled by suitable restricting or constraining means known to those skilled in the art such that the rigid frame 52 is only capable of moving in the direction of the actuating force. Since the anvil roll 44 is connected to the anvil support frame 54, the force is transmitted to the anvil roll 44 to press the substrate webs 12 and 14 against the outer peripheral bonding surface 24 of the bonding roll 20.

As representatively shown in the aspect of the invention illustrated in FIG. 3A, the bonding axis 22 can also be offset by a distance 94 from the anvil axis 44 such that the bonding axis 22 is not in a linear relationship with a line of force extending from the actuating force through the anvil axis 44. Applicants have found that such an arrangement is more stable than when the line of force extends directly through the bonding axis 22. Desirably, the bonding axis 22 is offset from the line of force by a distance 94 of from about 0.1 to about 7 centimeters and more desirably from about 0.5 to about 5 centimeters. In addition, the angle 96, as representatively illustrated in FIG. 3A, between the line of force and the anvil axis 44 and bonding axis 22 should be from about 0.3 to about 45 degrees and desirably from about 5 to about 30 degrees.

The different aspects of the present invention advantageously provide an apparatus and method for rotary bonding. The present invention includes an anvil roll which is capable of self-aligning or pivoting such that its surface remains substantially parallel to the bonding surface. In such a configuration, the anvil roll is capable of maintaining a substantially constant force on the bonding surface 24 of the bonding roll 20 across the entire anvil width 43 of the anvil roll 40. For example, the anvil roll 40 may maintain an average force on the bonding surface 24 of the bonding roll 20 of from about 1 to about 300 pounds per lineal inch (from about 0.1 to about 55 kilograms per lineal centimeter) across the anvil width 43 of the anvil roll 40. As used herein, the term "average" refers to the sum of the tested quantities divided by the total number of tested quantities.

The different aspects of the present invention can provide a substantially constant bond area percentage between the webs. As used herein, the term "bond area percentage" refers to the percentage of the total area of the two continuously moving webs which is bonded together. For example, as representatively illustrated in FIG. 2C, the bond area percentage would be calculated by determining the area of the substrate webs 12 and 14 which is actually bonded together, dividing the bonded area by the total area of the substrate webs and then multiplying the result by 100.

The substrate webs produced using the anvil roll of the different aspects of the present invention have a bond area which is substantially the same as the area of the bond pattern on the anvil roll. Moreover, the webs have a substantially constant mean bond area percentage which has a standard deviation of from about 0 to about 5 and desirably from about 0 to about 1. The webs also have a bond area percentage which has a coefficient of variability of less than 10, and desirably less than 5. As used herein, the term "mean" refers to the sum of the tested quantities divided by the total number of tested quantities. As used herein, the term "standard deviation" refers to the square root of the average of the squares of the deviations of the tested quantities from the average of the tested quantities. As used herein, the term "coefficient of variability" refers to the standard deviation of the mean bond area percentage divided by the mean bond area percentage. Substrate webs produced using the conventional, rigidly mounted anvils have had a much more variable bond area percentage.

Further, the mean bond area percentage of substrate webs bonded together using the anvil roll of the different aspects of the present invention is substantially greater than the mean bond area percentage of substrate webs bonded together using rigidly mounted anvils under similar operating conditions. For example, the mean bond area percentage of substrate webs bonded together using the anvil roll of the different aspects of the present invention is at least about 105 percent and desirably from about 110 to about 300 percent of the mean bond area percentage of substrate webs bonded together using rigidly mounted anvils under similar operating conditions.

In addition, substrate webs bonded together using the anvil roll of the different aspects of the present invention have a coefficient of variability which is substantially less than the coefficient of variability of substrate webs bonded together using rigidly mounted anvils. For example, the substrate webs bonded together using the anvil roll of the different aspects of the present invention have a coefficient of variability which is at least less than 75 percent and desirably less than 50 percent of the coefficient of variability of substrate webs bonded together using rigidly mounted anvils under similar operating conditions.

Thus, the different aspects of the invention can more efficiently provide an apparatus and method for bonding at least two continuously moving substrate webs together. The different aspects of the present invention provides more consistent bonds than conventional methods which use rigid anvil rolls because the anvil roll 40 is allowed to self-align or pivot to maintain contact with the bonding roll and to maintain a substantially constant force across the anvil width 43 of the anvil roll 40.

Figure 4:
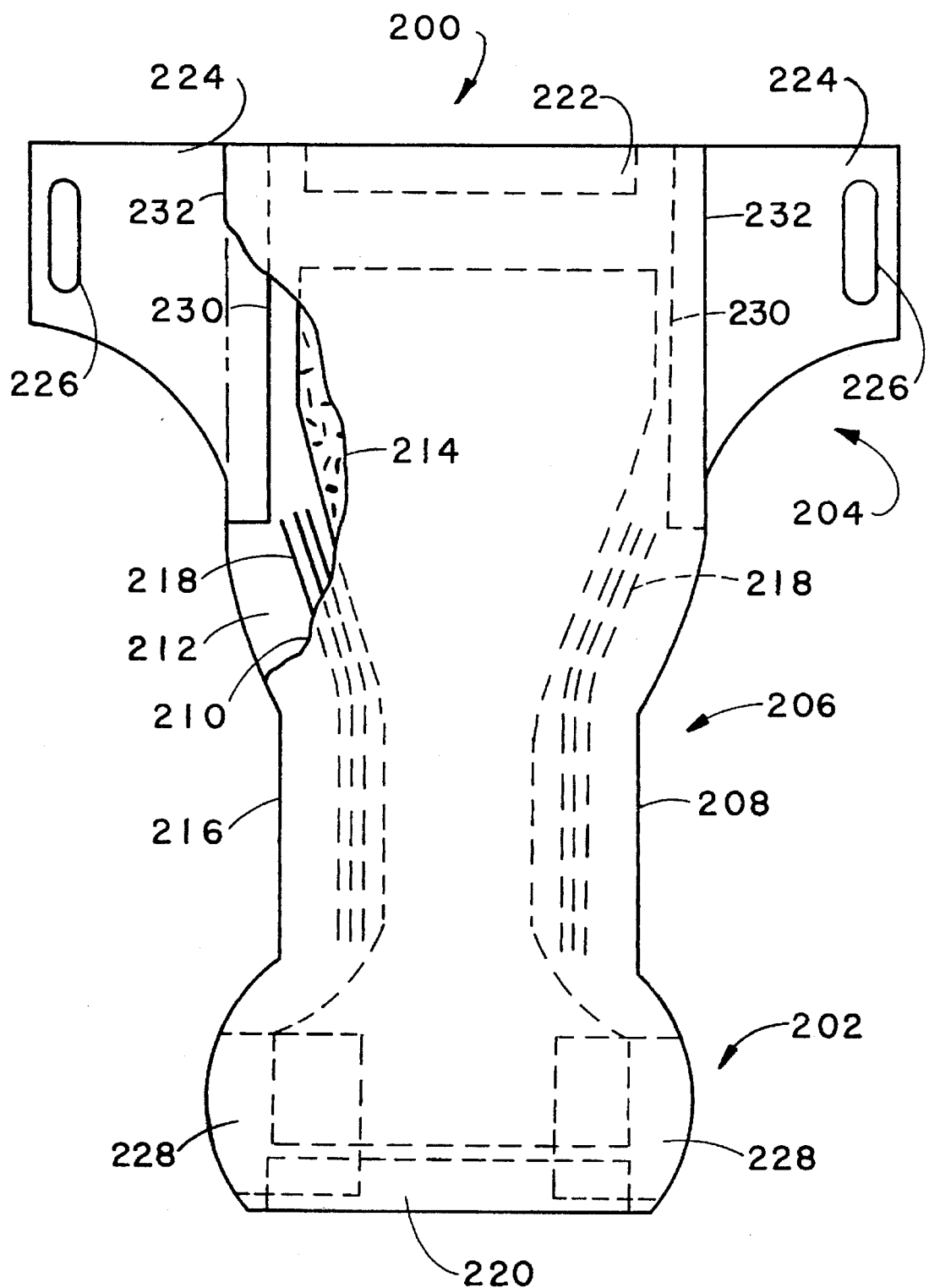
FIG. 4 representatively shows an absorbent article which is manufactured using the apparatus and method of the present invention.

The different aspects of the present invention may be used in the manufacture of an absorbent article, such as a disposable diaper which is representatively illustrated in FIG. 4. The absorbent article 200 defines a front portion 202, a rear portion 204, and a crotch portion 206 connecting the front portion 202 and the rear portion 204. The absorbent article 200 includes a bodyside liner 210, an outer cover 212, and an absorbent core 214 located between the bodyside liner 210 and the outer cover 212. As used herein, reference to a front portion refers to that part of the absorbent article which is generally located on the front of a wearer when in use. Reference to the rear portion refers to the portion of the article generally located at the rear of the wearer when in use, and reference to the crotch portion refers to that portion which is generally located between the legs of the wearer when in use.

The crotch portion 206 has opposite longitudinal side portions 208 which include a pair of elasticized, longitudinally extending leg cuffs 216. The leg cuffs 216 are generally adapted to fit about the legs of a wearer when in use and serve as a mechanical barrier to the lateral flow of body exudates. The leg cuffs 216 are elasticized by a pair of leg elastics 218. The absorbent article 200 further includes a front waist elastic 220 and a rear waist elastic 222. The rear portion 204 of the absorbent article 200 may further include a pair of stretchable ears 224 attached thereto which are adapted, in use, to overlap with the front portion 202 of the absorbent article 200. A fastening means such as snap closures, hook and loop fasteners, mushroom fasteners or tape fasteners may be attached to the stretchable ears 224 for releasably attaching the ears 224 to the front portion 202 of the absorbent article 200. The fastening means is intended to hold the absorbent article 200 about the waist of the wearer when in use. For example, a hook material 226 may be attached to the stretchable ears 224 and a mating loop material 228 may be attached to the front portion 202 of the absorbent article 200.

In a particular aspect, the stretchable ears 224 are attached to the back portion 204 of the absorbent article 200 using the various aspects of the method and apparatus of the present invention. For example, the proximate edge 230 of the stretchable ears 224 may be ultrasonically bonded to the absorbent article 200 along the lateral edges 232 of the back portion 204 of the absorbent article using the apparatus and method representatively illustrated in FIGS. 3A and 3B. The proximal edges 230 may be sandwiched between the outer cover 212 and bodyside liner 210 of the absorbent article 200 and ultrasonically bonded together. In such a configuration, the materials used for the outer cover 212, bodyside liner 210 and stretchable ears 224 must be compatible with ultrasonic bonding techniques. By using the rotary ultrasonic horn 32 and the anvil roll 40 of the present invention, a more consistent and higher quality bond is obtained between the stretchable ear 224 and the outer cover 212 and bodyside liner 210 because the anvil surface 42 and bonding surface 24 are maintained in a substantially parallel contacting relationship (FIGS. 3A and 3B).

The apparatus and method of the different aspects of the present invention may also be used to attach the fastening means to the absorbent article 200. For example, the apparatus and method as representatively illustrated in FIGS. 3A and 3B may be used to attach the hook material 226 to the stretchable ears 224.

The bodyside liner 210 of the absorbent article 200, as representatively illustrated in FIG. 4, suitably presents a body-facing surface which is compliant, soft feeling, and non-irritating to the wearer's skin. Further, the bodyside liner 210 may be less hydrophilic than the absorbent core 214, to present a relatively dry surface to the wearer, and may be sufficiently porous to be liquid permeable, permitting liquid to readily penetrate through its thickness. A suitable bodyside liner 210 may be manufactured from a wide selection of web materials such as porous foams, reticulated foams, apertured plastic films, natural fibers (for example, wood or cotton fibers), synthetic fibers (for example, polyester or polypropylene fibers), or a combination of natural and synthetic fibers. The bodyside liner 210 is suitably employed to help isolate the wearer's skin from liquids held in the absorbent core 214.

Various woven and nonwoven fabrics can be used for the bodyside liner 210. For example, the bodyside liner may be composed of a meltblown or spunbonded web of polyolefin fibers. The bodyside liner 210 may also be a bonded carded web composed of natural and/or synthetic fibers. The bodyside liner 210 may be composed of a substantially hydrophobic material, and the hydrophobic material may, optionally, be treated with a surfactant or otherwise processed to impart a desired level of wettability and hydrophilicity. In a particular aspect of the present invention, the bodyside liner 210 comprises a nonwoven, spunbond, polypropylene fabric composed of about 2.8–3.2 denier fibers formed into a web having a basis weight of about 22 grams per square meter and a density of about 0.06 grams per cubic centimeter. The fabric is surface treated with about 0.28 weight percent of a surfactant commercially available from Rohm and Haas Company under the trade designation Triton X-102.

The outer cover 212 of the absorbent article 200, as representatively illustrated in FIG. 4, may suitably be composed of a material which is either liquid permeable or liquid impermeable. It is generally preferred that the outer cover 212 be formed from a material which is substantially impermeable to liquids. For example, a typical outer cover can be manufactured from a thin plastic film or other flexible liquid impermeable material. For example, the outer cover 212 may be formed from a polyethylene film having a thickness of from about 0.012 millimeter (0.5 mil) to about 0.051 millimeter (2.0 mils). If it is desired to present the outer cover 212 with a more cloth-like feeling, the outer cover 212 may comprise a polyethylene film having a nonwoven web laminated to the outer surface thereof, such as a spunbond web of polyolefin fibers. For example, a polyethylene film having a thickness of about 0.015 millimeter (0.6 mil) may have thermally laminated thereto a spunbond web of polyolefin fibers, which fibers have a thickness of about 1.5 to 2.5 denier per filament, which nonwoven web has a basis weight of about 24 grams per square meter (0.7 ounces per square yard). Methods of forming such cloth-like outer covers are well known to those skilled in the art.

Further, the outer cover 212 may be formed of a woven or nonwoven fibrous web layer which has been totally or partially constructed or treated to impart a desired level of liquid impermeability to selected regions that are adjacent or proximate the absorbent core 214. Still further, the outer cover 212 may optionally be composed of a microporous "breathable" material which permits vapors to escape from the absorbent core 214 while still preventing liquid exudates from passing into the outer cover 212.

The absorbent core 214 of the absorbent article 200, as representatively illustrated in FIG. 4, is adapted to absorb body exudates. Any material capable of performing such a function is believed suitable for use in the present invention. The absorbent core 214 may comprise a single, integral piece of material or, alternatively, may comprise a plurality of individual, separate pieces of material which are operably assembled together. The absorbent core 214 may be manufactured in a wide variety of shapes and sizes (for example, rectangular, trapezoidal, T-shaped, I-shaped, hourglass shaped, etc.), and from a wide variety of materials. The size and the absorbent capacity of the absorbent core 214 should be compatible with the size of the intended wearer and the liquid loading imparted by the intended use of the absorbent article 200. The size and the absorbent capacity of the absorbent core 214 can be varied to accommodate wearers ranging from infants through adults. It is generally preferred that the absorbent core 214 be narrower in the crotch portion 206 of the absorbent article 200 than in the front or rear portion, 202 or 204, respectively.

Various types of wettable hydrophilic fibrous material can be used to form the absorbent core 214. Examples of suitable fibers include naturally occurring organic fibers composed of intrinsically wettable material, such as cellulosic fibers; synthetic fibers composed of cellulose or cellulose derivatives, such as rayon fibers; inorganic fibers composed of inherently wettable material, such as glass fibers; synthetic fibers made from inherently wettable thermoplastic polymers, such as particular polyester or polyamide fibers; and synthetic fibers composed of nonwettable thermoplastic polymer, such as polypropylene fibers, which have been hydrophilized by appropriate means. The fibers may be hydrophilized, for example, by treatment with silica, treatment with a material which has a suitable hydrophilic moiety and is not readily removable from the fiber, or by sheathing the nonwettable, hydrophobic fiber with a hydrophilic polymer during or after the formation of the fiber. For the purposes of the present invention, it is contemplated that selected blends of the various types of fibers mentioned above may also be employed. As used herein, the term "hydrophilic" describes fibers or the surface of fibers, which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 surface force analyzer system. When measured with this system, fibers having contact angles less than 90 degrees are designated "wettable", while fibers having contact angles greater than 90 degrees are designated "nonwettable".

In addition to the fibrous material described above, the absorbent core 214 may suitably comprise a high-absorbency material such as those known in the art as "superabsorbents". As a general rule, the high absorbency material is present in the absorbent core 214 in an amount of from about 5 to about 100 weight percent based on total weight of the absorbent core to provide more effective performance. High-absorbency materials can be natural, synthetic, and modified natural polymers and materials. In addition, the high-absorbency materials can be inorganic materials such as silica gels, or organic compounds such as crosslinked polymers. The term "crosslinked" refers to any means for effectively rendering normal water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic high-absorbency materials include polymeric materials, such as alkali metal and ammonium salts of poly(acrylic acid) and poly(methacrylic acid), poly(acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Other suitable absorbent gelling material s are disclosed by Assarson et al. in U.S. Pat. No. 3,902,236 issued Aug. 26, 1975. Processes for preparing synthetic, absorbent gelling polymers are disclosed in U.S. Pat. No. 4,076,663 issued Feb. 28, 1978, to Masuda et al. and U.S. Pat. No. 4,286,082 issued Aug. 25, 1981, to Tsubakimoto et al.

The high-absorbency material may be in any of a wide variety of geometric forms. As a general rule, it is preferred that the high-absorbency material be in the form of discrete particles. However, the high-absorbency material may also be in the form of fibers, flakes, rods, spheres, needles, or the like.

The outer cover 212 and bodyside liner 210 are generally adhered to one another so as to form a pocket in which the absorbent core 214 is located. Thus, the leg cuffs 216 are suitably formed by portions of the outer cover 212, and/or bodyside liner 210, which extend beyond the longitudinal sides of the absorbent core 214. Naturally, the leg cuffs 216 can also be formed from separate materials which are attached to the outer cover 212 and/or bodyside liner 210.

The leg cuffs 216, as representatively illustrated in FIG. 4, include leg elastics 218. Materials suitable for use in forming the leg elastics 218 are known to those skilled in the art. For example, the leg elastics 218 may include a plurality of elastic strands, such as, for example, Lycra® elastomeric strands available from DuPont, a business having offices in Wilmington, Del. The elastic strands are typically within the range of 470–1500 decitex. The leg elastics 218 may be generally straight or optionally curved. Similarly, the waist elastics 220 and 222 are well known to those skilled in the art.

A wide variety of diaper configurations, as well as training pants, incontinence garments, and like configurations, can be manufactured using the different aspects of the method and apparatus of the present invention. Suitable diapers are described in greater detail in following U.S. patents and patent applications, the disclosures of which are incorporated herein by reference in a manner that is consistent herewith: U.S. patent application Ser. No. 07/757,760 filed Sep. 11, 1991, in the name of Hanson et al; U.S. Pat. No. 4,149,335 issued Sep. 22, 1992, to Kellenberger et al.; U.S. Pat. No. 4,798,603 issued Jan. 17, 1989, to Meyer et al.; U.S. Pat. No. 4,704,116 issued Nov. 3, 1987 to Enloe; U.S. Pat. No. 5,147,343 issued Sep. 15, 1992, to Kellenberger; U.S. patent application Ser. No. 07/997,800 filed Dec. 29, 1992, in the name of McCormack et al., and U.S. patent application Ser. No. 08/148,130 filed Nov. 5, 1993, in the name of Dilnik et al.

The following examples provide a more complete understanding of the different aspects of the present invention and are not intended to limit the scope of the invention.

EXAMPLES

Figure 5A:
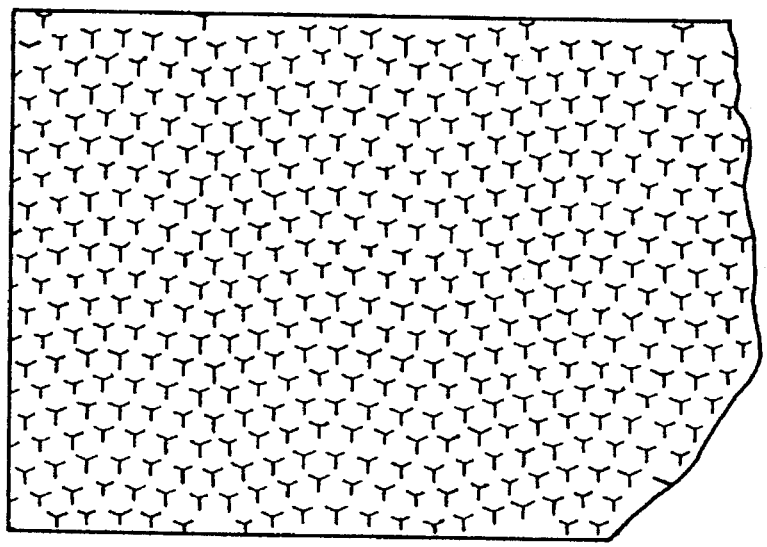
FIG. 5A representatively shows an example of a bond pattern which may be used on the anvil roll of the different aspects of the present invention.

The apparatus 10, as representatively illustrated in FIGS. 3A and 3B, was used to provide imprints on nip impression paper as the bond pattern and force between the anvil roll 40 and bonding roll 20 were varied. The imprints were used to provide a comparison of the bond quality and consistency obtained when using the self-aligning anvil roll 40 of the different aspects of the present invention versus a fixed anvil roll. Two anvil rolls 40 Which have two different bond patterns were used. The first anvil roll 40 had a diameter of 5.89 inches (15.0 centimeters) and had bond pattern A as representatively illustrated in FIG. 5A. The second anvil roll 40 had a diameter of 5.25 inches (13.3 centimeters) and had bond pattern B as representatively illustrated in FIG. 5B. Each anvil roll 40 had a width of 4.0 inches (10.16 centimeters) with the corresponding bond pattern extending completely across the width of the anvil roll. The actuating force exerted between the anvil roll 40 and the bonding roll 20 was controlled such that imprints were made with actuating forces of 40 psi (pounds per square inch), 50 psi and 60 psi. The force translates into a normalized force of 10 pli (pounds per lineal inch), 12.5 pli and 15 pli, respectively, across the surface of each anvil roll 40 (11.52, 14.40 and 17.28 kilograms per lineal centimeter, respectively).

Example 1

As representatively illustrated in FIGS. 3A and 3B, the first anvil roll 40 which had bond pattern A was used in conjunction with a rotary ultrasonic bonding roll 20 or horn to provide the imprint on the nip impression paper. The anvil roll 40 was fixed by adjusting the pivot stops 70 to maintain the anvil roll 40 in a desired position. The pressuring means 90 exerted a force of 40 psi such that the anvil roll exerted a force of 10 pli (11.52 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed to determine the bond area percentage. For the purposes of the Examples, the term "bond area percentage" refers to the percentage of the total area of the impression paper which was actually imprinted. The bond area percentage of the impression paper approximates the actual bond area percentage which would occur when bonding two substrate webs together. The bond area percentage was calculated by determining the area of the impression paper which was actually imprinted, dividing the imprinted area by the total area of the paper and then multiplying the result by 100.

The impression paper was viewed through a 20 MM Nikon lens from a height of 90 centimeters with 4 flood lamps directed at the impression paper. The bond area percentage of the impression paper was then determined using a Quantimet 970 Image Analyzer which is commercially available from Leica Instruments, Inc., a company having business offices located in Deerfield, Ill. The image analyzer was equipped with version 8.0 software which is also available from Leica Instruments, Inc. A length of the imprint was divided into 40 equal frames of about 0.56 centimeters in width. The image analyzer determined the mean bond area percentage for each frame by differentiating between the darkened or imprinted areas and the lighter or nonimprinted areas. The mean bond area percentage and standard deviation for all of the frames was then determined. The imprint had a mean bond area percentage of 6.53 percent with a standard deviation of 0.84. The imprint also had a coefficient of variability of 12.9.

Example 2

The first anvil roll 40 which had bond pattern A was used again in conjunction with a rotary ultrasonic bonding roll 20 or horn to provide an imprint on the nip impression paper. The anvil roll 40 was fixed by adjusting the pivot stops 70 to maintain the anvil roll 40 in a desired position. The pressuring means 90 exerted a force of 50 psi such that the anvil roll exerted a force of 12.5 pli (14.40 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 8.27 percent with a standard deviation of 1.45. The imprint also had a coefficient of variability of 17.5.

Example 3

The first anvil roll 40 which had bond pattern A was used again in conjunction with a rotary ultrasonic bonding roll 20 or horn to provide an imprint on the nip impression paper. The anvil roll 40 was fixed by adjusting the pivot stops 70 to maintain the anvil roll 40 in a desired position. The pressuring means 90 exerted a force of 60 psi such that the anvil roll exerted a force of 15.0 pli (17.28 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 11.70 percent with a standard deviation of 3.32. The imprint also had a coefficient of variability of 28.4.

Example 4

The first anvil roll 40 which had bond pattern A was used again in conjunction with a rotary ultrasonic bonding roll 20 or horn to provide the imprint on the nip impression paper. However, the anvil roll 40 was allowed to self-align with the bonding roll 20 by adjusting the pivot stops 70 to allow the anvil roll 40 to pivot. Thus, the surface of the anvil roll 40 maintained a substantially parallel relationship with the surface of the bonding roll 20. The pressuring means 90 exerted a force of 40 psi such that the anvil roll exerted a force of 10.0 pli (11.52 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 15.70 percent with a standard deviation of 0.43. The imprint also had a coefficient of variability of 2.7.

Example 5

The first anvil roll 40 which had bond pattern A was used again in conjunction with a rotary ultrasonic bonding roll 20 or horn to provide an imprint on the nip impression paper.

As in Example 4, the anvil roll 40 was allowed to self-align with the bonding roll 20 by adjusting the pivot stops 70 to allow the anvil roll 40 to pivot. Thus, the surface of the anvil roll 40 maintained a substantially parallel relationship with the surface of the bonding roll 20. The pressuring means 90 exerted a force of 50 psi such that the anvil roll exerted a force of 12.5 pli (14.40 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 16.10 percent with a standard deviation of 0.62. The imprint also had a coefficient of variability of 3.9.

Example 6

The first anvil roll 40 which had bond pattern A was used again in conjunction with a rotary ultrasonic bonding roll 20 or horn to provide an imprint on the nip impression paper. As in Example 4, the anvil roll 40 was allowed to self-align with the bonding roll 20 by adjusting the pivot stops 70 to allow the anvil roll 40 to pivot. Thus, the surface of the anvil roll 40 maintained a substantially parallel relationship with the surface of the bonding roll 20. The pressuring means 90 exerted a force of 60 psi such that the anvil roll exerted a force of 15.0 pli (17.28 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 17.80 percent with a standard deviation of 0.46. The imprint also had a coefficient of variability of 2.6.

Example 7

Figure 5B:
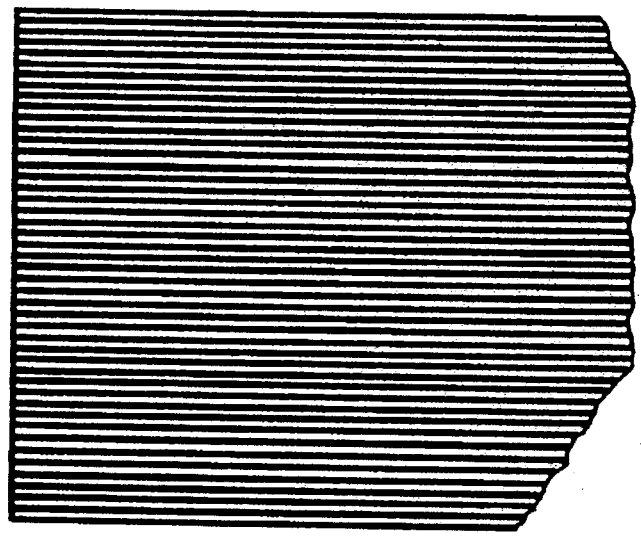
FIG. 5B representatively shows an example of another bond pattern which may be used on the anvil roll of the different aspects of the present invention.

The second anvil roll 40 which had bond pattern B, as representatively illustrated in FIG. 5B, was used in conjunction with a rotary ultrasonic bonding roll 20 or horn to provide an imprint on the nip impression paper. The anvil roll 40 was fixed by adjusting the pivot stops 70 to maintain the anvil roll 40 in a desired position. The pressuring means 90 exerted a force of 40 psi such that the anvil roll exerted a force of 10.0 pli (11.52 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 21.5 percent with a standard deviation of 6.6. The imprint also had a coefficient of variability of 30.7.

Example 8

The second anvil roll 40 which had bond pattern B was used in conjunction with a rotary ultrasonic bonding roll 20 or horn to provide an imprint on the nip impression paper. The anvil roll 40 was fixed by adjusting the pivot stops 70 to maintain the anvil roll 40 in a desired position. The pressuring means 90 exerted a force of 50 psi such that the anvil roll exerted a force of 12.5 pli (14.40 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 25.0 percent with a standard deviation of 7.1. The imprint also had a coefficient of variability of 28.4.

Example 9

The second anvil roll 40 which had bond pattern B was used again in conjunction with a rotary ultrasonic bonding roll 20 or horn to provide an imprint on the nip impression paper. The anvil roll 40 was fixed by adjusting the pivot stops 70 to maintain the anvil roll 40 in a desired position. The pressuring means 90 exerted a force of 60 psi such that the anvil roll exerted a force of 15.0 pli (17.28 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 27.1 percent with a standard deviation of 3.2. The imprint also had a coefficient of variability of 11.8.

Example 10

The second anvil roll 40 which had bond pattern B was used again in conjunction with a rotary ultrasonic bonding roll 20 or horn to provide an imprint on the nip impression paper. However, the anvil roll 40 was allowed to self-align with the bonding roll 20 by adjusting the pivot stops 70 to allow the anvil roll 40 to pivot. Thus, the surface of the anvil roll 40 maintained a substantially parallel relationship with the surface of the bonding roll 20. The pressuring means 90 exerted a force of 40 psi such that the anvil roll exerted a force of 10.0 pli (11.52 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 34.0 percent with a standard deviation of 1.3. The imprint also had a coefficient of variability of 3.8.

Example 11

The second anvil roll 40 which had bond pattern B was used again in conjunction with a rotary ultrasonic bonding roll 20 or horn to provide an imprint on the nip impression paper. As in Example 10, the anvil roll 40 was allowed to self-align with the bonding roll 20 by adjusting the pivot stops 70 to allow the anvil roll 40 to pivot. Thus, the surface of the anvil roll 40 maintained a substantially parallel relationship with the surface of the bonding roll 20. The pressuring means 90 exerted a force of 50 psi such that the anvil roll exerted a force of 12.5 pli (14.40 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 34.4 percent with a standard deviation of 1.3. The imprint also had a coefficient of variability of 3.8.

Example 12

The second anvil roll 40 which had bond pattern B was used again in conjunction with a rotary ultrasonic bonding roll 20 or horn to provide an imprint on the nip impression paper. As in Example 10, the anvil roll 40 was allowed to self-align with the bonding roll 20 by adjusting the pivot stops 70 to allow the anvil roll 40 to pivot. Thus, the surface of the anvil roll 40 maintained a substantially parallel relationship with the surface of the bonding roll 20. The pressuring means 90 exerted a force of 60 psi such that the anvil roll exerted a force of 15.0 pli (17.28 kilograms per lineal centimeter) between the bonding roll 20 and anvil roll 40. The rotary ultrasonic bonding roll 20 was rotated such that the impression paper was moved at about 17 feet per minute (5 meters per minute) between the bonding roll 20 and the fixed anvil roll 40. The contact between the anvil roll 40 and the bonding roll 20 caused an imprint to be made on the nip impression paper.

The imprint was analyzed as described in Example 1 to determine the bond area percentage of each frame and the mean bond area percentage and standard deviation for all of the frames. The imprint had a mean bond area percentage of 35.4 percent with a standard deviation of 1.2. The imprint also had a coefficient of variability of 3.4.

Figure 6:
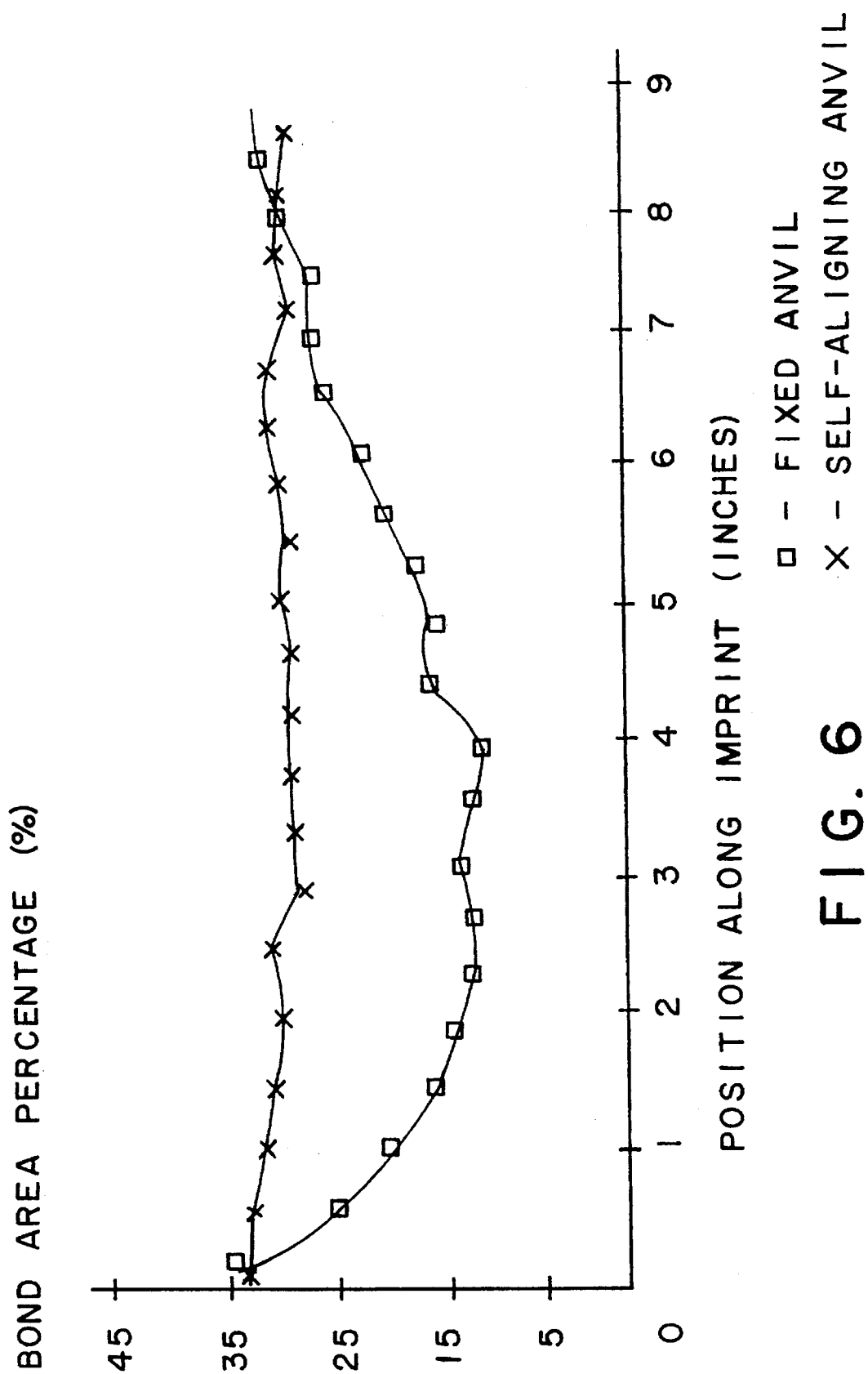
FIG. 6 representatively shows a graph comparing the different bond area percentages achieved using a fixed or rigid anvil roll versus the anvil roll of the different aspects of the present invention.

The data obtained from the examples was tabulated in Tables 1 and 2. FIG. 6 representatively shows a graph which compares the bond area percentage achieved in Example 7 (Fixed anvil roll) with that achieved in Example 10 (Self-aligning anvil roll) along a specified length of the imprint. As illustrated in FIG. 6 and Tables 1 and 2, the imprints made using the self-aligning anvil roll of the different aspects of the present invention were more consistent and more accurately reflect the bond pattern used on the anvil roll than the imprints made using the fixed anvil roll. For example, when using bond pattern A, the imprints produced using the anvil roll of the different aspects of the present invention had a bond area percentage which was from 15.70 to 17.80 percent with a standard deviation of from 0.43 to 0.62. Whereas, when using bond pattern A, the imprints produced using the conventional, rigidly mounted or fixed anvil rolls had a bond area percentage which was from 6.53 to 11.70 percent with a standard deviation of from 0.84 to 3.32. In addition, when using bond pattern B, the imprints produced using the anvil roll of the different aspects of the present invention had a bond area percentage which was from 34.0 to 35.4 percent with a standard deviation of from 1.2 to 1.3. Whereas, when using bond pattern B, the imprints produced using the conventional, rigidly mounted or fixed anvil rolls had a bond area percentage which was from 21.5 to 27.1 percent with a standard deviation of from 3.2 to 7.1. Thus, bonding with conventional fixed anvils resulted in a much lower and more variable bond area percentage which did not accurately reflect the bond pattern on the anvil roll.

While the invention has been described in detail with respect to specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

TABLE 1

BOND PATTERN A

|  | Ex. No. | Load (psi) | Bond Area % | Standard Deviation | Variability = S.D./BA % |
|---|---|---|---|---|---|
| Fixed Anvil | 1 | 40 | 6.53 | 0.84 | 12.9 |
|  | 2 | 50 | 8.27 | 1.45 | 17.5 |
|  | 3 | 60 | 11.70 | 3.32 | 28.4 |
| Self-Aligning Anvil | 4 | 40 | 15.70 | 0.43 | 2.7 |
|  | 5 | 50 | 16.10 | 0.62 | 3.9 |
|  | 6 | 60 | 17.80 | 0.46 | 2.6 |

TABLE 2

BOND PATTERN B

|  | Ex. No. | Load (psi) | Bond Area % | Standard Deviation | Variability = S.D./BA % |
|---|---|---|---|---|---|
| Fixed Anvil | 7 | 40 | 21.5 | 6.6 | 30.7 |
|  | 8 | 50 | 25.0 | 7.1 | 28.4 |
|  | 9 | 60 | 27.1 | 3.2 | 11.8 |
| Self-Aligning Anvil | 10 | 40 | 34.0 | 1.3 | 3.8 |
|  | 11 | 50 | 34.4 | 1.3 | 3.8 |
|  | 12 | 60 | 35.4 | 1.2 | 3.4 |

What is claimed is:

1. A method for bonding at least two continuously moving substrate webs together comprising the steps of:

a) supplying at least two continuously moving substrate webs along a substrate path;

b) providing a rotatable bonding roll adjacent said substrate path wherein said bonding roll has an outer peripheral bonding surface upon which said substrate webs travel;

c) rotating said bonding roll about a bonding axis;

d) providing a rotatable anvil roll adjacent said substrate path wherein said anvil roll has an outer peripheral anvil surface and an anvil width and wherein said anvil roll rotates about an anvil axis and presses said substrate webs against said bonding surface of said bonding roll thereby bonding said substrate webs together; and e) pivotally supporting said anvil roll about a pivot axis to continuously align said anvil axis to maintain said anvil surface in a substantially parallel relationship with said bonding surface of said bonding roll wherein said pivot axis is located a first distance from said bonding axis and said anvil axis is located a second distance from said bonding axis wherein said second distance is greater than said first distance.

2. The method of claim 1 wherein the step of supplying said substrate webs includes the step of supplying at least one nonwoven material.

3. The method of claim 1 wherein the step of supplying said substrate webs includes the step of supplying at least one elastomeric material.

4. The method of claim 1 wherein said step of providing a rotatable bonding roll comprises the step of providing an ultrasonic bonding means which includes a rotary ultrasonic horn.

5. The method of claim 1 wherein said step of providing said rotatable anvil roll comprises the step of providing a plurality of projections on said anvil surface of said anvil roll to bond said substrate webs together at bond locations which are arranged in a predetermined bond pattern which has a width of at least about 1 centimeter.

6. The method of claim 1 wherein said steps of providing said rotatable anvil roll and pivotally supporting said anvil roll maintain a substantially constant bond area percentage between said substrate webs.

7. The method of claim 6 wherein said bond area percentage between said substrate webs has a standard deviation of from about 0 to about 5.

8. The method of claim 1 wherein said step of pivotally supporting said anvil roll includes the step of maintaining a substantially constant force on said bonding surface of said bonding roll substantially across said anvil width of said anvil roll.

9. The method of claim 1 wherein said step of pivotally supporting said anvil roll comprises the step of providing an anvil support frame which is pivotally connected to a rigid frame at two pivot points located on said pivot axis wherein said anvil roll and said anvil support frame pivot about said pivot axis to maintain said anvil surface in said substantially parallel relationship with said bonding surface.

* * * * *